(12) United States Patent
Mills et al.

(10) Patent No.: US 11,389,548 B2
(45) Date of Patent: *Jul. 19, 2022

(54) ORAL FOOD CHALLENGE MEAL FORMULATIONS

(71) Applicant: Reacta Biotech Limited, Manchester (GB)

(72) Inventors: Clare Mills, Altrincham (GB); Anuradha Balasundaram, Manchester (GB); Carol Ann Costello, Manchester (GB); Ivona Baricevic-Jones, Stockport (GB)

(73) Assignee: Reacta Biotech Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/576,465

(22) PCT Filed: Jun. 3, 2016

(86) PCT No.: PCT/GB2016/051637
§ 371 (c)(1),
(2) Date: Nov. 22, 2017

(87) PCT Pub. No.: WO2016/193744
PCT Pub. Date: Dec. 8, 2016

(65) Prior Publication Data
US 2018/0177895 A1 Jun. 28, 2018

(30) Foreign Application Priority Data
Jun. 4, 2015 (GB) .................................... 1509718

(51) Int. Cl.
| | | |
|---|---|---|
| A61K 9/00 | (2006.01) | |
| A61K 49/00 | (2006.01) | |
| A23G 1/30 | (2006.01) | |
| A23L 29/212 | (2016.01) | |
| A23L 27/00 | (2016.01) | |
| A23L 29/30 | (2016.01) | |
| A23L 5/40 | (2016.01) | |
| A23L 33/00 | (2016.01) | |
| A23L 33/10 | (2016.01) | |
| A61K 39/35 | (2006.01) | |
| A23L 7/10 | (2016.01) | |
| A23L 19/00 | (2016.01) | |
| A23L 9/10 | (2016.01) | |
| A23L 35/00 | (2016.01) | |

(52) U.S. Cl.
CPC ............ *A61K 49/0004* (2013.01); *A23G 1/30* (2013.01); *A23L 5/40* (2016.08); *A23L 7/198* (2016.08); *A23L 9/10* (2016.08); *A23L 19/01* (2016.08); *A23L 27/84* (2016.08); *A23L 29/212* (2016.08); *A23L 29/35* (2016.08); *A23L 33/00* (2016.08); *A23L 33/10* (2016.08); *A23L 33/30* (2016.08); *A23L 35/00* (2016.08); *A61K 39/35* (2013.01); *A23V 2002/00* (2013.01)

(58) Field of Classification Search
CPC ....... A61K 49/0004; A23G 1/30; A23L 29/35; A23L 5/40; A23L 33/30; A23L 27/84; A23L 33/10
See application file for complete search history.

(56) References Cited

U.S. PATENT DOCUMENTS

| | | | | |
|---|---|---|---|---|
| 2002/0037357 | A1* | 3/2002 | Fritsche | A23J 3/343 426/656 |
| 2013/0149670 | A1* | 6/2013 | Francois | A61K 8/0208 433/216 |
| 2015/0343075 | A1* | 12/2015 | Raff | A61P 43/00 424/489 |
| 2016/0263212 | A1* | 9/2016 | Friedman | A61K 31/445 |
| 2016/0287656 | A1* | 10/2016 | Abdul Majid | A61K 9/0007 |

FOREIGN PATENT DOCUMENTS

| | | |
|---|---|---|
| JP | S5480463 A | 6/1979 |
| JP | H07134125 A | 5/1995 |
| JP | 3294693 B2 | 6/2002 |
| KR | 20100091270 A | 8/2010 |

OTHER PUBLICATIONS

JP-3294693-B2 May 23, 1995—Translation document.*
Roquette Pharma Products, KLEPTOSE Linecaps: Taste-Masking Solution, Mar. 26, 2014. downloaded online (Year: 2014).*
Kent Precision Foods, Foothill Farms Neutral Mousse Instant Mix, downloaded online Nov. 7, 2019.*
Preis et al., "A comparative study on solubilizing and taste-masking capacities of hydroxypropyl-[beta]-cyclodextrin and maltodextrins with high amylose con," Sensors and Actuators B: Chemical: International Journal Devoted to Research and Development of Physical and Chemical Transducers, Elsevier BV, NL, vol. 193, Dec. 8, 2013, pp. 442-450, XP028818847, ISSN: 0925-4005.
Cochrane et al., "Development of a standardized low-dose double-blind placebo-controlled challenge vehicle for the EuroPrevall project," Allergy, vol. 67, No. 1, Sep. 19, 2011, pp. 107-113, XP055286521, United Kingdom, ISSN: 0105-4538.
Vummaneni et al., "Taste Masking Technologies: An Overview and Recent Updates," International Journal of Research in Pharmaceutical and Biomedical Sciences, vol. 3, No. 2, Jun. 1, 2012, pp. 510-524, XP055286144, ISSN: 2229-3701.
International Search Report and the Written Opinion dated Jul. 14, 2016 for corresponding International Application No. PCT/GB2016/051637, filed Jul. 14, 2016, 15 pgs.
Bock, et al., "Double-blind, placebo-controlled food challenge (DBPCFC) as an office procedure: a manual." The Journal of Allergy and Clinical Immunology, 82, Dec. 1988, pp. 986-997.
Ingelfinger, et al., "Gastrointestinal Allergy," The New England Journal of Medicine, vol. 241, Jul.-Dec. 1949, pp. 337-340.

(Continued)

*Primary Examiner* — Susan T Tran
(74) *Attorney, Agent, or Firm* — Shumaker & Sieffert, P.A.

(57) ABSTRACT

This invention relates to kits including novel oral food challenge meal formulations. In particular, the invention also relates to kits including novel oral food challenge meal formulations, wherein the placebo dose formulation is indistinguishable from non-placebo dose formulations.

12 Claims, No Drawings

(56) References Cited

OTHER PUBLICATIONS

Niggemann, et al., "Pitfalls in double-blind, placebo-controlled oral food challenges," Allergy, 62, pp. 729-732, Mar. 2007.
Sampson, et al., Standardizing double-blind, placebo-controlled oral food challenges: American Academy of Allergy, Asthma & Immunology-European Academy of Allergy and Clinical Immunology, PRACTALL Consensus Report, The Journal of Allergy and Clinical Immunology, 130, Dec. 2012; pp. 1260-1274.
Vassilopoulou, et al., "Evaluation and standarisation of different matrices used for double-blind placebo-controlled food challenges to fish," Journal of human nutrition and dietetics: the office journal of the British Dietetic Association 23, pp. 544-549, 2010.
Vlieg-Boerstra, et al., "Development and validation of challenge materials for double-blind, placebo-controlled food challenges in children," The Journal of Allergy and Clinical Immunology, 112, pp. 341-346, Feb. 2004.
Ronteltap, et al., "Sensory testing of receipes masking peanut or hazelnut for double-blind placebo-controlled food challenges," Allergy, 59, pp. 457-460, 2004.
Mackie, et al., "High fat food increases gastric residence and thus thresholds for objective symptoms in allergic patients," Molecular nutrition and food research, 56, pp. 1708-1714, 2012.
Ballmer-Weber et al., "How much is too much? Threshold dose distributions for 5 food allergens," The Journal of Allergy and clinical immunology, 135, pp. 964-971, Apr. 2015.
Combined Search and Examination Report from counterpart Great Britain Application No. 1509718.1, dated Dec. 7, 2015, 9 pp.
Opinion of the Scientific Panel on Dietetic Products, Nutrition and Allergies on wheat-based maltodextrins, European Food Safety Authority, The EFSA Journal (2007) 487, May 3, 2007, 7 pp.
Bock, "Oral Food Challenges in an Office Setting," Retrieved from: http://www.aaifnc.org/Documents/symposium_2014/Dr.%20S.%20Allan%20Bock.pdf, accessed Mar. 12, 2015, 40 pp.

\* cited by examiner

ORAL FOOD CHALLENGE MEAL FORMULATIONS

This application is a national stage application under 35 U.S.C. § 371 of PCT Application No. PCT/GB2016/051637, filed Jun. 3, 2016, which claims the benefit of Great Britain Application No. 1509718.1, filed Jun. 4, 2015. The entire contents of each of PCT Application No. PCT/GB2016/051637 and Great Britain Application No. 1509718.1 are incorporated herein by reference in their entirety.

TECHNICAL FIELD

This invention relates to kits including novel oral food challenge meal formulations.

BACKGROUND

Oral food challenges are generally considered to be the gold-standard for diagnosis of food related adverse reactions to foods, including IgE-mediated reactions, especially when performed in a double-blind, placebo-controlled fashion[1]. The original concept was described in 1949 at which time it was suggested that food should be given in such a way that the patient is unaware of its nature[2].

Oral food challenges are usually undertaken to confirm whether an individual has a clinical allergy and can drive treatment plans including elimination diets and food avoidance, as well as prescription of rescue medication should a patient inadvertently consume a problem food[3]. There have been several position papers on diagnosis of food allergy which have focused primarily on the clinical aspects of undertaking double blind placebo controlled food challenges (DBPCFC), culminating in the recently published PRAC-TALL consensus paper[4].

Much effort has focused in the clinical community on harmonising clinical protocols and stopping criteria but little consideration has been given to standardisation of the agents and food vehicles used for food challenges, or for dose verification. A key attribute of a food allergen challenge is to blind or mask the flavour and texture of the "active" allergenic food, to provide a placebo dose (without allergen) and active dose (containing allergenic ingredient) where the patient cannot tell which dose they are being given. This has resulted in a plethora of different approaches and recipes, includes various cooked and baked products, cakes and milks shakes, and different methods to assess the efficacy of blinding, including triangle testing, a sensory test used by the food industry to compare products[5-7].

It is generally accepted that allergenic foods should be used in their usual edible form and this was the approach that was adopted in the EuroPrevall project. In the EuroPrevall project, a chocolate dessert base formulation was developed which was capable of blinding a variety of commercially available dry powdered food ingredients and is an ambient shelf-life stable product by virtue of its low water activity[8, 9]. This was done to ease the issues of cost-effective shipping and shelf-life requirements for the multi-centre, transnational project. The matrix has been used to collect a variety of challenge data including peanut, hazelnut, celery spice (celeriac) and fish powder[10]. It is reconstituted at the point of use by addition of potable water, stored chilled (2-8° C.) and used within 24 h of rehydration. To date challenge meal formulations have generally fallen short of the requirement of blinding or masking the flavour and texture of the "active" allergenic food. For example, the EuroPrevall project describes that, although hazelnut allergen was successfully masked, the same could not be said for celeriac as 30/37 panelists (i.e. 81%) without nose clips and 27/35 panelists (i.e. 77%) were able to correctly identify the difference between the placebo sample and the 'high-allergen' sample. The panelists in this study reported the 'high-allergen' dessert as having a more 'grainy', less 'smooth' texture and less 'sweet', more 'bitter' taste and, consequently, less 'chocolate' flavour.

SUMMARY OF THE DISCLOSURE

It is an aim of the present invention to provide an oral food challenge meal formulation having taste-masking properties for an allergen present in the formulation.

It is also an aim of the present invention to provide an oral food challenge meal formulation having texture-masking properties for an allergen present in the formulation.

It is also an aim of the present invention to provide an oral food challenge meal formulation having taste-masking properties such that a challenge meal formulation containing an allergen is indistinguishable from a challenge meal formulation in which the allergen is absent (i.e. a placebo challenge meal formulation).

It is also an aim of the present invention to provide an oral food challenge meal formulation having texture-masking properties such that a challenge meal formulation containing an allergen is indistinguishable from a challenge meal formulation in which the allergen is absent (i.e. a placebo challenge meal formulation).

The present invention achieves one or more, e.g. all, of the above listed aims.

The disclosure relates to kits including novel oral food challenge meal formulations, wherein the placebo dose formulation is indistinguishable from non-placebo dose formulations. The disclosure also relates to novel oral food challenge meal formulations, to methods of using the kits and the novel oral food challenge meal formulations and to a use of an additive compound to improve the properties of an oral food challenge meal formulation. In particular, the disclosure relates to novel oral food challenge meal formulations having improved taste and/or texture masking properties for the allergen contained in the formulation.

In accordance with the present invention there is provided a kit comprising:
a challenge meal formulation comprising no food allergen (i.e. a placebo challenge meal formulation); and
a challenge meal formulation comprising allergen of up to about 10% w/w (i.e. a non-placebo challenge meal formulation);
wherein the challenge meal formulations comprise an additive present in an amount of up to about 1.5% w/w of the oral food challenge meal formulation, wherein the additive is selected from the group consisting of: maltodextrin, dextrin, cyclodextrin and combinations thereof.

In accordance with the present invention there is also provided an oral food challenge meal formulation comprising an additive present in an amount of up to about 1.5% w/w of the oral food challenge meal formulation, wherein the additive is selected from the group consisting of: maltodextrin, dextrin, cyclodextrin and combinations thereof.

The kits and oral food challenge meal formulations of the present invention differ from conventional oral challenge meal formulations in that the formulation includes an additive selected from the group consisting of: maltodextrin, dextrin, cyclodextrin and combinations thereof. Thus, the original formulation developed for the EuroPrevall project[8] has been modified to allow inclusion of increased amounts of allergenic ingredient whilst maintaining blinding (e.g. texture and/or taste blinding). A key aspect of the new invention is being able to manipulate the texture of the placebo and active doses to enable them to be matched.

In accordance with the present invention there is provided a method of diagnosing a food allergy comprising:
a) administering to a subject a challenge meal formulation of the invention comprising no food allergen (a placebo challenge meal formulation); or a challenge meal formulation of the invention comprising allergen (a non-placebo challenge meal formulation), wherein the presence or absence of food allergen in the challenge meal formulation is not known to the subject;
b) monitoring for an allergic response;
c) grading the allergic response;
d) repeating steps a) to c) with a different challenge meal formulation until all challenge meal formulations have been administered;
e) correlating the graded allergic response with the known level of food allergen; and
f) diagnosing whether or not the subject has a food allergy.

In accordance with the present invention there is provided a use of an additive in a challenge meal formulation, wherein the additive is selected from the group consisting of maltodextrin, dextrin, cyclodextrin and combinations thereof, for masking taste and/or texture properties of an allergen present in the challenge meal formulation.

In accordance with the present invention there is provided a use of an additive in a challenge meal formulation of a kit comprising a placebo dose formulation and a non-placebo dose formulation, wherein the additive is selected from the group consisting of maltodextrin, dextrin, cyclodextrin and combinations thereof, the use being to make the placebo dose formulation indistinguishable from the non-placebo dose formulation.

In accordance with the present invention there is provided a use of an additive selected from the group consisting of maltodextrin, dextrin, cyclodextrin and combinations thereof for masking taste and/or texture properties of an allergen present in the challenge meal formulation such that a challenge meal formulation containing an allergen is indistinguishable from a challenge meal formulation in which the allergen is absent (i.e. a placebo challenge meal formulation).

DETAILED DESCRIPTION OF THE DISCLOSURE

Kits Comprising Placebo and Non-Placebo Oral Food Challenge Meal Formulations:

In accordance with the present invention there is provided a kit comprising:
a challenge meal formulation comprising no food allergen (i.e. a placebo challenge meal formulation); and
a challenge meal formulation comprising allergen of up to about 10% w/w (i.e. a non-placebo challenge meal formulation);
wherein the challenge meal formulations comprise an additive present in an amount of up to about 1.5% w/w of the oral food challenge meal formulation, wherein the additive is selected from the group consisting of: maltodextrin, dextrin, cyclodextrin and combinations thereof.

In an embodiment, the kit of the present invention comprises: (i) a challenge meal formulation comprising no food allergen, wherein the challenge meal formulation comprises from about 0.05% w/w to about 1.5% w/w additive; and (ii) a challenge meal formulation comprising up to 10% w/w (e.g. about 0.5% w/w to about 10% w/w) of allergen, wherein the challenge meal formulation comprises from about 0.05% w/w to about 1.5% w/w additive. Preferably, the presence or absence of food allergen in the challenge meal formulation is not known to the subject.

In line with the teaching of the present invention, in a kit comprising a placebo dose formulation and an allergen containing formulation, the presence of the additive in the placebo dose formulation matches the texture of this formulation with the texture of the allergen containing formulation (such that the placebo and allergen containing formulation are indistinguishable).

In accordance with the present invention there is provided a kit of the present invention for use in diagnosing a food allergy.

In an embodiment, the challenge meal formulation of the kit of the invention further comprises: a matrix formation component; a texturizing component (i.e. a texture compensating component); and a flavour/colour masking component. The additive component (i.e. the maltodextrin, dextrin and/or cyclodextrin) component of the challenge meal formulation of the kit of the invention may be, but is not necessarily, described as being a part of the texture compensatory component.

In an embodiment, the challenge meal formulation of the kit of the invention further comprises an allergen component. Formulations comprising an allergen component are non-placebo formulations. In an alternate embodiment, the challenge meal formulation of the kit of the invention does not include an allergen component. Formulations not including an allergen component are placebo formulations.

Additive Component (i.e. Maltodextrin, Dextrin and/or Cyclodextrin Component):

In an embodiment, the additive component is present in the challenge meal formulation in an amount of no more than about 1.5% w/w; no more than about 1.4% w/w; no more than about 1.3% w/w; no more than about 1.2% w/w; no more than about 1.1% w/w; no more than about 1.0% w/w; no more than about 0.9% w/w; no more than about 0.8% w/w; no more than about 0.7% w/w; no more than about 0.6% w/w; or no more than about 0.5% w/w.

In an embodiment, the additive component is present in the challenge meal formulation in an amount of more than 0.05% w/w. In an embodiment, the additive component is present in the challenge meal formulation in an amount of more than 0.1% w/w.

Preferably, the additive component is present in the challenge meal formulation in an amount of from about 0.05% w/w to about 1.5% w/w. More preferably, the additive component is present in the challenge meal formulation in an amount of from about 0.05% w/w to about 1.0% w/w. More preferably, the additive component is present in the challenge meal formulation in an amount of from about 0.05% w/w to about 0.5% w/w. The additive component may be present in the challenge meal formulation in an amount of from about 0.05% w/w to about 0.4% w/w, from about 0.05% w/w to about 0.3% w/w, from about 0.1% w/w to about 0.5% w/w or from about 0.2% w/w to about 0.5% w/w.

The amount of additive component in the challenge meal formulation is important as this is determinate of the texture of the formulation (e.g. by the degree of emulsification, stability and/or homogeneity of the formulation).

In an embodiment, the additive component comprises maltodextrin. In an alternate embodiment, the additive component comprises dextrin. In an alternate embodiment, the additive component comprises cyclodextrin.

Preferably the additive component comprises maltodextrin. Preferably, the maltodextrin is present in the formulation in an amount of from about 0.05% w/w to about 0.5% w/w.

Matrix Formation Component:

In an embodiment, the matrix formation component is present in the formulation in an amount of from about 20% w/w to about 60% w/w; from about 25% w/w to about 55% w/w; or from about 30% w/w to about 50% w/w.

In an embodiment, the matrix formation component comprises a starch component and sucrose.

In an embodiment, the starch component of the matrix formation component comprises a cold swelling starch or a pregelatinised modified starch. Preferably, a cold swelling starch as cold hydrating viscosifying agent is employed as the starch component of the matrix formation component. In a preferred embodiment of the cold swelling starch is selected from the group consisting of: Ultratex 2™, Ultratex 2000™, Ultratex 3™, Ultratex 4™, Ultratex SR™, Ultratex HV™, Instant Clearjel™, Ultrasperse 3™ Ultrasperse-™IMF, Ultrasperse 5™, Ultrasperse A™, NOVATION Endura 0100, NOVATION Prima 300, NOVATION 8300, NOVATION 3300, NOVATION 9230, NOVATION 9330, and combinations thereof. Most preferably the starch component of the matrix formation component is Ultratex 4™. The mentioned examples are available from Ingredion.

In an embodiment, the starch component is present in the formulation in an amount of from about 10% w/w to about 25% w/w. The starch component may be present in the formulation in an amount of from about 10% w/w to about 24% w/w, from about 10% w/w to about 23% w/w, from about 10% w/w to about 22% w/w, from about 10% w/w to about 21% w/w, from about 10% w/w to about 20% w/w or from about 10% w/w to about 19% w/w. The starch component may be present in the formulation in an amount of from about 11% w/w to about 25% w/w, from about 12% w/w to about 25% w/w, from about 13% w/w to about 25% w/w or from about 14% w/w to about 25% w/w. Preferably, the starch component is present in the formulation in an amount of from about 14% w/w to about 19% w/w.

In an embodiment, the sucrose component is present in the formulation in an amount of from about 15% w/w to about 30% w/w. The sucrose component may be present in the formulation in an amount of from about 15% w/w to about 29% w/w, from about 15% w/w to about 28% w/w, from about 15% w/w to about 27% w/w or from about 15% w/w to about 26% w/w. The sucrose component may be present in the formulation in an amount of from about 16% w/w to about 30% w/w, from about 17% w/w to about 30% w/w, from about 18% w/w to about 30% w/w or from about 19% w/w to about 30% w/w. Preferably, the sucrose component is present in the formulation in an amount of from about 18% w/w to about 28% w/w. More preferably, the sucrose component is present in the formulation in an amount of from about 19% w/w to about 26% w/w.

Preferably the matrix formation component comprises sucrose and Ultratex 4™. Preferably, the sucrose is present in the formulation in an amount of from about 19% w/w to about 26% w/w and the Ultratex 4™ is present in the formulation in an amount of from about 14% w/w to about 19% w/w.

Texturizing Component:

As mentioned above, the additive component (i.e. the maltodextrin, dextrin and/or cyclodextrin) component of the formulation may be, but is not necessarily, described as being a part of the texturizing component (i.e. texture compensatory component).

In an embodiment, the texturizing component is present in the formulation in an amount of from about 10% w/w to about 35% w/w; from about 15% w/w to about 30% w/w; or from about 20% w/w to about 25% w/w.

In an embodiment, the texturizing component comprises an oil component and a surfactant.

In an embodiment, the oil component of the texturizing component comprises a fat or fat blends selected from the group consisting of: highly refined, bleached and deodorised oils. Preferably, the oil component of the texturizing component is selected from the group consisting of: maize oil, sunflower oil, rapeseed oil, corn oil, low melting fats and combinations thereof. In an embodiment, the oil component of the texturising component is a non-allergenic species and of non-dairy origin. Preferably, the oil component of the texturizing component comprises highly refined oil or maize oil.

In an embodiment, the oil component is present in the formulation in an amount of from about 15% w/w to about 30% w/w. The oil component may be present in the formulation in an amount of from about 15% w/w to about 29% w/w, from about 15% w/w to about 28% w/w, from about 15% w/w to about 27% w/w, from about 15% w/w to about 26% w/w or from about 15% w/w to about 25% w/w. The oil component may be present in the formulation in an amount of from about 16% w/w to about 30% w/w, from about 17% w/w to about 30% w/w, from about 18% w/w to about 30% w/w, from about 19% w/w to about 30% w/w or about 20% w/w to about 30% w/w. Preferably, the oil component is present in the formulation in an amount of from about 20% w/w to about 25% w/w. More preferably, the oil component is present in in the formulation in an amount of from about 21% w/w to about 24% w/w. Still more preferably, the oil component is present in in the formulation in an amount of from about 22% w/w to about 24% w/w. Most preferably, the oil component is present in in the formulation in an amount of from about 22% w/w to about 23% w/w.

In an embodiment, the surfactant component of the texturizing component is selected from the group consisting of: lecithin, polyglycerol polyricinoleate, monoglycerides, distilled monoglycerides, citric acid esters of monoglycerides, di-acetyl acetic acid esters of monoglycerides, lactic acid esters of monoglyceride, diglycerides, polyglycerol esters of fatty acids or sorbitan esters of fatty acids and polyoxyethylene compositions such as sorbitan monopolyoxyethylene (Tween). Preferably, the surfactant component of the texturizing component is selected from the group consisting of: lecithin and a polyoxyethylene composition, such as sorbitan monopolyoxyethylene (Tween). Most preferably, the surfactant component of the texturizing component is Polysorbate 60.

In an embodiment, the surfactant component is present in the formulation in an amount of from about 0.1% w/w to about 2% w/w. The surfactant component may be present in the formulation in an amount of from about 0.1% w/w to about 1.8% w/w, from about 0.1% w/w to about 1.6% w/w, from about 0.1% w/w to about 1.4% w/w, from about 0.1% w/w to about 1.2% w/w or from about 0.1% w/w to about 1.0% w/w. The surfactant component may be present in the formulation in an amount of from about 0.2% w/w to about 2% w/w, from about 0.3% w/w to about 2% w/w, from about 0.4% w/w to about 2% w/w or from about 0.5% w/w to about 2% w/w. Preferably, the surfactant component is present in the formulation in an amount of from about 0.5% w/w to about 1.0% w/w. More preferably, the surfactant component is present in the formulation in an amount of from about 0.5% w/w to about 0.9% w/w. Still more preferably, the surfactant component is present in the formulation in an amount of from about 0.5% w/w to about 0.8% w/w. Yet still more preferably, the surfactant component is present in the formulation in an amount of from about 0.5% w/w to about 0.7% w/w. Most preferably, the surfactant component is present in the formulation in an amount of from about 0.5% w/w to about 0.6% w/w.

Preferably the texturizing component comprises Polysorbate 60 and highly refined oil or maize oil. Preferably, the Polysorbate 60 is present in the formulation in an amount of from about 0.5% w/w to about 0.6% w/w and the highly refined oil or maize oil is present in the formulation in an amount of from about 22% w/w to about 23% w/w.

Flavour/Colour Masking Component:

In an embodiment, the flavour/colour masking component is present in the formulation in an amount of from about 10% w/w to about 45% w/w; from about 15% w/w to about 40% w/w; or from about 20% w/w to about 35% w/w.

In an embodiment, the flavour/colour masking component comprises a highly coloured sweet food powder, a grain component and a liquid (e.g. oil) or powder based flavouring selected from the group consisting of: banana, pineapple, cherry, blackcurrant, raspberry, strawberry, blackberry, blueberry, cranberry, plum, coconut, guava, red apple, pear, mango, apricot, peach, chocolate, cocoa, caramel, toffee, molasses, condensed milk, butterscotch, buttery, bubble gum, fudge, cotton candy, vanilla, coffee, cinnamon, ice cream, honey, custard and combinations thereof.

In an embodiment, the highly coloured sweet food powder of the flavour/colour masking component is selected from the group consisting of: cocoa, tomato, beetroot, carrot and carob powders. Preferably, the highly coloured sweet food powder of the flavour/colour masking component is cocoa or tomato powder. Most preferably, the highly coloured sweet food powder of the flavour/colour masking component is cocoa powder.

In an embodiment, the highly coloured sweet food powder is present in the formulation in an amount of from about 15% w/w to about 30% w/w. The highly coloured sweet food powder may be present in the formulation in an amount of from about 15% w/w to about 29% w/w, from about 15% w/w to about 28% w/w, from about 15% w/w to about 27% w/w, from about 15% w/w to about 26% w/w or from about 15% w/w to about 25% w/w. The highly coloured sweet food powder may be present in the formulation in an amount of from about 16% w/w to about 30% w/w, from about 17% w/w to about 30% w/w, from about 18% w/w to about 30% w/w or from about 19% w/w to about 30% w/w. Preferably, the highly coloured sweet food powder is present in the formulation in an amount of from about 19% w/w to about 25% w/w.

In an embodiment, the grain component is present in the formulation in an amount of from about 1% w/w to about 10% w/w. The grain component may be present in the formulation in an amount of from about 1% w/w to about 9% w/w, from about 1% w/w to about 8% w/w or from about 1% w/w to about 7% w/w. The grain component may be present in the formulation in an amount of from about 2% w/w to about 10% w/w or from about 3% w/w to about 10% w/w. Preferably, the grain component is present in the formulation in an amount of from about 3% w/w to about 8% w/w.

In an embodiment, the grain component is selected from the group consisting of: oatmeal, a triticale family grain (e.g. wheat, barley or spelt) and maize. Preferably, the grain component is oatmeal. In an embodiment, the oatmeal is toasted oatmeal. In an embodiment, the oatmeal is ground oatmeal. Ground oatmeal is prepared by milling the oatmeal to a particle size of about 0.1 to 1 mm, preferably 0.3 to 0.8 mm and most preferably about 0.5 mm. In an embodiment, the oatmeal is toasted and ground oatmeal. Toasted and ground oatmeal (prepared by toasting fine oatmeal and then milling about 0.5 mm) yields a fine, hard and gritty meal which has a sweet and nutty flavour. This component is particularly useful in challenge meal formulations including peanut allergen.

In an embodiment, the liquid or powder based flavouring is present in the formulation in an amount of from about 0.1% w/w to about 3% w/w; from about 0.3% w/w to about 2.5% w/w; or from about 0.5% w/w to about 2.0% w/w. The liquid or powder based flavouring may be present in the formulation in an amount of from about 0.1% w/w to about 2.4% w/w; from about 0.1% w/w to about 2.3% w/w; from about 0.1% w/w to about 2.2% w/w; from about 0.1% w/w to about 2.1% w/w; from about 0.1% w/w to about 2.0% w/w; from about 0.1% w/w to about 1.9% w/w; or from about 0.1% w/w to about 1.8% w/w. The liquid or powder based flavouring may be present in the formulation in an amount of from about 0.2% w/w to about 2.5% w/w; from about 0.3% w/w to about 2.5% w/w; from about 0.4% w/w to about 2.5% w/w; from about 0.5% w/w to about 2.5% w/w; from about 0.6% w/w to about 2.5% w/w; from about 0.7% w/w to about 2.5% w/w; or from about 0.8% w/w to about 2.5% w/w. Preferably, the liquid or powder based flavouring is present in the formulation in an amount of from about 0.8% w/w to about 1.8% w/w.

In an embodiment, the liquid or powder based flavouring comprises a chocolate flavoured powder. In an embodiment, the liquid or powder based flavouring comprises a chocolate flavoured powder in combination with one or more of the liquid or powder based flavourings mentioned above.

Preferably the flavour/colour masking component comprises cocoa powder, oatmeal and a liquid or powder based flavouring. Preferably, the cocoa powder is present in the formulation in an amount of from about 19% w/w to about 25% w/w, the oatmeal is present in the formulation in an amount of from about 3% w/w to about 8% w/w and the liquid or powder based flavouring is present in the formulation in an amount of from about 0.8% w/w to about 1.8% w/w. Preferably the oatmeal is toasted and ground oatmeal.

Allergen Component:

In an embodiment, the formulation further comprises an allergen component. Formulations comprising an allergen component are non-placebo formulations. In an alternate embodiment, the formulation does not include an allergen component. Formulations not including an allergen component are placebo formulations.

In formulations comprising an allergen component the allergen component is present in the formulation in an amount of up to about 10% w/w. It has been found in triangle testing experiments that formulations containing larger quantities of allergen component much more difficult to mask in terms of taste and/or texture.

In an embodiment, the allergen component is selected from the group consisting of: peanut, soy, egg, sesame seeds, milk (e.g. cows milk), fish, crustaceans, almond, cashew, hazelnut, pistachio, walnut, sulphites, wheat, mustard and celery allergen. In a preferred embodiment, the allergen component is peanut allergen.

In an embodiment, the allergen component is present in the formulation in an amount of from about 0.5% w/w to about 10% w/w, preferably from about 1% w/w to about 10% w/w.

In an embodiment, the allergen component is present in the formulation in an amount of from about 1% w/w to about 9% w/w; about 1% w/w to about 8% w/w; about 1% w/w to about 7% w/w; about 1% w/w to about 6% w/w; about 1% w/w to about 5% w/w; about 1% w/w to about 4% w/w; about 1% w/w to about 3% w/w; or about 1% w/w to about 2% w/w allergen component.

Method of Diagnosing a Food Allergy:

In accordance with the present invention there is provided a method of diagnosing a food allergy comprising:

a) administering to a subject a challenge meal formulation of the invention comprising (i) no food allergen (a placebo challenge meal formulation); or (ii) a challenge meal formulation of the invention comprising allergen (a non-placebo challenge meal formulation), wherein the presence or absence of food allergen in the challenge meal formulation is not known to the subject;

b) monitoring for an allergic response;

c) grading the allergic response;

d) repeating steps a) to c) with a different challenge meal formulation until all challenge meal formulations have been administered;

e) correlating the graded allergic response with the known level of food allergen; and f) diagnosing whether or not the subject has a food allergy.

In an embodiment, step (a) of the method of diagnosing a food allergy comprises administering to a subject (i) a challenge meal formulation comprising no food allergen, wherein the challenge meal formulation comprises from about 0.05% w/w to about 1.5% w/w additive; and (ii) a challenge meal formulation comprising up to 10% w/w (e.g. about 1% w/w to about 10% w/w) of allergen, wherein the challenge meal formulation comprises from about 0.05% w/w to about 1.5% w/w additive; wherein the presence or absence of food allergen in the challenge meal formulation is not known to the subject.

Definitions

For the avoidance of doubt, it is hereby stated that the information disclosed earlier in this specification under the heading "Background" is relevant to the invention and is to be read as part of the disclosure of the invention.

Throughout this specification, whenever a specific value is quoted for a temperature, pressure or time, the temperature, pressure or time quoted is approximate rather than the precise temperature, amount of pressure or amount of time. Nevertheless, the disclosure includes the precise value of any such variables which are approximately that value.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

1 Bock, S. A. et al. Double-blind, placebo-controlled food challenge (DBPCFC) as an office procedure: a manual. *The Journal of allergy and clinical immunology* 82, 986-997 (1988).

2 Ingelfinger, F. J., Lowell, F. C. & Franklin, W. Gastrointestinal allergy. *The New England journal of medicine* 241, 337; passim, doi:10.1056/nejm194909012410905 (1949).

3 Niggemann, B. & Beyer, K. Pitfalls in double-blind, placebo-controlled oral food challenges. *Allergy* 62, 729-732, doi:10.1111/j. 1398-9995.2007.01396.x (2007).

4 Sampson, H. A. et al. Standardizing double-blind, placebo-controlled oral food challenges: American Academy of Allergy, Asthma & Immunology-European Academy of Allergy and Clinical Immunology PRACTALL consensus report. *The Journal of allergy and clinical immunology* 130, 1260-1274, doi:10.1016/j.jaci.2012.10.017 (2012).

5 Vassilopoulou, E. et al. Evaluation and standardisation of different matrices used for double-blind placebo-controlled food challenges to fish. *Journal of human nutrition and dietetics: the official journal of the British Dietetic Association* 23, 544-549, doi:10.1111/j.1365-277X.2010.01046.x (2010).

6 Vlieg-Boerstra, B. J. et al. Development and validation of challenge materials for double-blind, placebo-controlled food challenges in children. *The Journal of allergy and clinical immunology* 113, 341-346, doi:10.1016/j.jaci.2003.10.039 (2004).

7 Ronteltap, A. et al. Sensory testing of recipes masking peanut or hazelnut for double-blind placebo-controlled food challenges. *Allergy* 59, 457-460 (2004).

8 Cochrane, S. A. et al. Development of a standardized low-dose double-blind placebo-controlled challenge vehicle for the EuroPrevall project. *Allergy* 67, 107-113, doi:10.1111/j.1398-9995.2011.02715.x (2012).

9 Mackie, A. et al. High fat food increases gastric residence and thus thresholds for objective symptoms in allergic patients. *Molecular nutrition & food research* 56, 1708-1714, doi:10.1002/mnfr.201200330 (2012).

10 Ballmer-Weber, B. K. et al. How much is too much? Threshold dose distributions for 5 food allergens. *The Journal of allergy and clinical immunology* 135, 964-971, doi:10.1016/j.jaci.2014.10.047 (2015).

EXAMPLES

The following examples provide various formulations falling within the scope of the present invention.

There is a fine balance between the amount of starch, maltodextrin, polysorbate, and maize oil which will determine the degree of emulsification and thus stability and homogeneity of the mixture.

The matrix formation is driven by the ability of Ultratex 4 (Starch, hydrogen phosphate, 2-hydroxypropyl ether, CAS 53124-00-8) to form a gel network on addition of water. The key aspect of the invention is the manipulation of the rheological properties of the gel network by the addition of maltodextrin in the placebo formulation to allow textural matching with the active.

Sensory properties of the following formulations have been evaluated by informal taste panels (n=4-8) to assess blinding with regards to texture. Attributes scored were identified regarding the organoleptic properties of the dessert. Little difference was perceived with regards odour and flavour attributes between the placebo and allergen containing formulations, including roasted nut flavours. Importantly, no trace of peanut could be discerned in the allergen containing formulations. With regards the texture, no difference in the thickness of the desserts was perceived and little variation in its smoothness, grittiness or astringent qualities could be discerned.

Example 1

The formulation comprises the following ingredients:

| Ingredient | Placebo formulation % (w/w) | Peanut formulation % (w/w) |
| --- | --- | --- |
| Peanut Flour | 0.00 | 0.67 |
| MaltoDextrin | 0.35 | 0.35 |
| Starch (Ultra-TEX-4) | 17.15 | 17.50 |
| Toasted Oatmeal | 7.67 | 7.67 |
| Alkalised Cocoa | 24.26 | 23.19 |
| Sucrose | 26.35 | 26.60 |
| Maize oil | 22.83 | 22.83 |
| Polysorbitan 60 | 0.60 | 0.60 |
| Orange oil | 0.79 | 0.59 |
| Total | 100.00 | 100.00 |

Example 2

The formulation comprises the following ingredients:

| | Placebo formulation (% w/w) | Peanut containing formulation (% w/w) |
| --- | --- | --- |
| Peanut Flour | 0.00 | 0.67 |
| Maltodextrin | 0.50 | 0.50 |
| Starch (Ultra-TEX-4) | 17.00 | 17.00 |
| Toasted Oatmeal | 7.67 | 7.67 |
| Alkalised Cocoa | 24.26 | 23.54 |
| Sucrose | 26.35 | 26.29 |
| Maize oil | 22.83 | 22.83 |
| Polysorbitan 60 | 0.60 | 0.60 |
| Fruit flavours | 0.79 | 0.90 |
| Total | 100.00 | 100.00 |

Example 3: Sensory Evaluation of Chocolate Mousse Containing Peanut Protein Using the Triangle Test Method for Similarity In order to diagnose the severity of a peanut allergy, a chocolate mousse product (with different peanut levels) was produced. Two samples of chocolate mousse: "Control" (placebo recipe containing no peanut protein) and "Test" (a recipe containing peanut at 0.67% w/w) were submitted for sensory evaluation using the Triangle Test Method TES-S-001 (for similarity) using a panel of 42 sensory assessors (selected from the Campden BRI Trained Triangle Test Panel).

The samples were submitted in powdered format. Prior to the test the samples were prepared by reconstitution with cold water (mains supply) by the following protocol:

Pots were stored at ambient temperature (≤25° C.), and out of direct sun light prior to reconstitution.

The dessert doses were produced in 300 g masses in 800 ml pots.

Each 300 g doses were reconstituted as a single dose.

Reconstitution was carried out with all placebo desserts first followed by all the peanut containing doses.

Water from the mains supply at Campden BRI was used to reconstitute.

After initial reconstitution the desserts were stored in a refrigerator between 2-8° C. overnight.

700 mls of water was measured out using a measuring jug.

100 mls of the measured water was poured into the pot containing the dry dessert and mixed with the spatula until fully absorbed.

The pots were then left at room temperature for 10 minutes.

The dessert was emptied into a Kenwood mixer (model number: Major KM230) with a paddle blade.

The remaining 600 mls of water was poured into the now empty dessert pot and residual dessert was dissolved by gentle mixing.

The desert matrix was them mixed on low speed for 2 minutes.

A further 100 mls of water was added and mixed on low speed for 2 minutes.

A third 100 mls of water was added and mixed on low speed for 2 minutes.

Then 200 mls of water was added and mixed on low speed for 2 minutes.

The remaining water was added and mixed on low speed for 2 minutes.

The final reconstituted dessert was emptied into a coded glass mixing bowl, covered with tin foil and refrigerated overnight.

The above protocol was repeated for each pot working initially with placebo and then onto the peanut containing dose.

Between batches all equipment was washed with hot water and detergent and then rinsed with copious amounts of clean water. All equipment was then dried prior to use.

The aim of the test was to determine whether the panel could perceive any sensory difference(s) between the two samples to determine whether the addition of the peanut protein is detectable.

The samples were placed into the applicable coded containers presented following the experimental design of the test. Each assessor received a heaped teaspoon of sample per coded container.

The samples were evaluated using the Triangle Test Procedure (TES-S-001). In the triangle test assessors are presented with a set of three coded samples, two of which are the same and one of which is different. The sets of samples are presented equally often in each of the six possible orders; this experimental design minimises any possible order and carryover effects.

Forty-two trained assessors are used for each test, twenty-one receiving "test" as the different sample and twenty-one receiving "control" as the different sample. After tasting the three samples in the designated order, each assessor is asked to select the "different" sample and to describe the difference(s) perceived.

The test was carried out in a purpose-built testing room. Each assessor was required to undertake the tests in an individual booth. The room was positively pressurised to minimise the entrance of external odours. Coloured lighting was used to mask any colour difference between the samples. The panel were instructed to palate cleanse with plain crackers and water (bottled) between the samples to minimise sample carry-over.

For a triangle test for similarity using 42 assessors, a maximum number of 16 correct responses are required to establish similarity between the two samples. The results show that 16 of the 42 assessors correctly identified the odd or different sample. It can therefore be concluded that the samples are statistically similar at the 5% Beta ($\beta$) and 30% Pd selected levels, that is, we are 95% confident that only 30% of discriminators can detect a difference.

Alpha ($\alpha$)—probability of concluding that a perceptible difference exists when one does not Beta ($\beta$)—probability of concluding that no perceptible difference exists when one does Pd—maximum allowable proportion of distinguishers Reference: Sensory Analysis Methodology—Triangle Test BS EN ISO 4120: 2007

On reviewing the descriptors recorded by the panel (who correctly identified the "odd" or "different" sample), two assessors described an almond-essence note in the Test sample. However no other descriptors related to the peanut flavour of the samples were recorded. The test results above indicate that the two samples are statistically similar at the selected levels (5% Beta ($\beta$) and 30% Pd) i.e. no significant difference was detected between the two chocolate mousse samples: Test (0.67% w/w peanut recipe) and Control (placebo recipe).

The invention claimed is:

1. A kit comprising:
   a placebo challenge meal dessert formulation comprising no food allergen; and
   a non-placebo challenge meal dessert formulation comprising food allergen of between about 0.5% w/w to about 10% w/w, based on the total weight of the non-placebo challenge meal dessert formulation, wherein the allergen component in the non-placebo challenge meal dessert formulation is selected from the group consisting of: peanut, soy, egg, sesame seeds, milk, fish, crustaceans, almond, cashew, hazelnut, pistachio, walnut, sulphites, wheat, mustard and celery allergen;
   wherein the placebo and the non-placebo challenge meal dessert formulations each comprise:
   20% w/w to 60% w/w of a matrix formation component, wherein the matrix formation component comprises a starch and sucrose,
   10% w/w to 35% w/w of a texturizing component, wherein the texturizing component comprises an oil and a surfactant,
   10% w/w to 45% w/w of a flavor/color masking component, and
   an additive present in an amount of from about 0.05% w/w to about 1.0% w/w, based on the total weight of each of the placebo and the non-placebo challenge meal dessert formulations, wherein the additive is selected from the group consisting of: maltodextrin, dextrin, and combinations thereof, and
   wherein, upon reconstitution with water, the placebo and the non-placebo challenge meal dessert formulations each form a mousse.

2. The kit of claim 1, wherein the allergen component in the non-placebo challenge meal dessert formulation is peanut allergen.

3. The kit of claim 1, wherein the additive is maltodextrin.

4. The kit of claim 1, wherein the starch comprises a cold swelling starch or a pre-gelatinized modified starch.

5. The kit of claim 1, wherein the sucrose is present in the placebo and the non-placebo challenge meal dessert formulations in an amount of from about 19% w/w to about 26% w/w, based on the total weight of each of the placebo and the non-placebo challenge meal dessert formulations, and the starch is present in the placebo and the non-placebo challenge meal dessert formulations in an amount of from about 14% w/w to about 19% w/w, based on the total weight of each of the placebo and the non-placebo challenge meal dessert formulations.

6. The kit of claim 1, wherein the oil of the texturizing component comprises highly refined oil or maize oil.

7. The kit of claim 1, wherein the surfactant component of the texturizing component is Polysorbate 60.

8. The kit of claim 1, wherein the surfactant is present in the placebo and the non-placebo challenge meal dessert formulations in an amount of from about 0.5% w/w to about 0.6% w/w, based on the total weight of each of the placebo and the non-placebo challenge meal dessert formulations, and the oil is present in the placebo and the non-placebo challenge meal dessert formulations in an amount of from about 22% w/w to about 23% w/w, based on the total weight of each of the placebo and the non-placebo challenge meal dessert formulations.

9. The kit of claim 1, wherein the flavor/color masking component comprises:
   cocoa or tomato powder,
   a grain, or
   a liquid or powder based flavoring selected from the group consisting of banana, pineapple, cherry, blackcurrant, raspberry, strawberry, blackberry, blueberry, cranberry, plum, coconut, guava, red apple, pear, mango, apricot, peach, chocolate, cocoa, caramel, toffee, molasses, condensed milk, butterscotch, buttery, bubble gum, fudge, cotton candy, vanilla, coffee, cinnamon, ice cream, honey, custard and combinations thereof.

10. The kit of claim 9, wherein the flavor/color masking component is a grain, and the grain is oatmeal.

11. The kit of claim 9, wherein the flavor/color masking component is a liquid or powder based flavoring, and the liquid or powder based flavoring is a chocolate flavored powder.

12. The kit of claim 9, wherein the cocoa or tomato powder is present in the placebo and the non-placebo challenge meal dessert formulations in an amount of from about 19% w/w to about 25% w/w, based on the total weight of each of the placebo and the non-placebo challenge meal dessert formulations, the grain is present in the placebo and the non-placebo challenge meal dessert formulations in an amount of from about 3% w/w to about 8% w/w, based on the total weight of each of the placebo and the non-placebo challenge meal dessert formulations, and the liquid or powder based flavoring is present in the placebo and the non-placebo challenge meal dessert formulations in an amount of from about 0.8% w/w to about 1.8% w/w, based on the total weight of each of the placebo and the non-placebo challenge meal dessert formulations.

* * * * *